United States Patent [19]

Alexander et al.

[11] Patent Number: 4,512,038

[45] Date of Patent: Apr. 23, 1985

[54] BIO-ABSORBABLE COMPOSITE TISSUE SCAFFOLD

[75] Inventors: Harold Alexander, Short Hills; John R. Parsons, Montclair; Irving D. Strauchler, Irvington; Andrew B. Weiss, Short Hills, all of N.J.

[73] Assignee: University of Medicine and Dentistry of New Jersey, Newark, N.J.

[21] Appl. No.: 251,285

[22] Filed: Apr. 6, 1981

Related U.S. Application Data

[62] Division of Ser. No. 033,945, Apr. 27, 1979, Pat. No. 4,329,743.

[51] Int. Cl.³ ............................................. A61F 1/00
[52] U.S. Cl. .................................... 3/1.9; 128/92 C; 128/92 B; 128/92 D
[58] Field of Search ............... 128/92 D, 334 R, 335.5; 428/105, 408, 110; 3/1, 1.9, 1.91

[56] References Cited

U.S. PATENT DOCUMENTS

| | | | |
|---|---|---|---|
| 3,272,204 | 9/1966 | Artandi et al. | 128/334 R |
| 3,276,448 | 10/1966 | Kronenthal | 128/334 |
| 3,463,158 | 8/1969 | Schmitt et al. | 3/1 |
| 3,526,906 | 9/1970 | Delaszlo | 128/92 C |
| 3,707,006 | 12/1972 | Bokros et al. | 3/1.9 |
| 3,738,906 | 6/1973 | Olcott | 3/1 X |
| 3,739,773 | 6/1973 | Schmitt et al. | 128/334 R X |
| 3,893,196 | 7/1975 | Hochman | 3/1.91 X |
| 3,992,725 | 11/1976 | Homsy | 428/408 |
| 4,164,045 | 8/1979 | Bokros et al. | 3/1.4 |
| 4,196,230 | 12/1978 | Gibson et al. | 428/408 |

OTHER PUBLICATIONS

"Polylaetic Acid for Surgical Implants", Kulkarni et al., Arch Surgery, vol. 93, pp. 839-843, Nov. 1, 1966.
"Induction of Tendon and Ligament Formation by Carbon Implants", Jenkins, et al., Journal of Bone and Joint Surgery, vol. 59B, pp. 53-57.

Primary Examiner—Richard J. Apley
Assistant Examiner—David J. Isabella
Attorney, Agent, or Firm—Dennis P. Clarke

[57] ABSTRACT

The invention comprises a bio-compatible composition suitable for constructing surgical articles for the repair or replacement of a part of the body of a human or non-human animal, e.g., ligaments, tendons, bones, comprising a composite of a bio-absorbable polymer and at least one substrate of a plurality of carbon fibers.

The invention also includes surgical articles fabricated from the composites for the repair of damaged tissue, e.g., tendons, ligaments and bones.

The invention includes a method for the formation of the aforesaid composite comprising providing a substrate of the carbon fibers and providing the substrate with a continuous coating of a bio-absorbable polymer.

The invention also includes the surgical repair of a damaged body part such as a ligament, tendon or bone comprising surgically affixing to the damaged part the surgical article, the bio-absorbable polymer being absorbed by the body upon formation of the new tissue.

18 Claims, 4 Drawing Figures

BIO-ABSORBABLE COMPOSITE TISSUE SCAFFOLD

This application is a division of application Ser. No. 033,945, filed Apr. 27, 1979, now U.S. Pat. No. 4,329,743.

BACKGROUND OF THE INVENTION

The treatment of injured ligaments and tendons remains a serious clinical problem. Inadequately repaired damage to these structures results in pain, loss of function, and in some cases, subsequent degenerative arthritis. When severely damaged by trauma or disease, fibrous tissue repair is often impossible. Many researchers have suggested the use of replacement structures for such damaged tissue. At this time, however, a completely successful prosthesis for use in a chronic implantation has not been developed.

Difficult fractures of the long bones often require an internal fixation device to maintain stability and alignment during healing. A rigid metallic plate is usually the device of choice, although, ideally, the stiffness of the plate should vary over the course of treatment. During early healing, rigid fixation by plating promotes primary osseous union. Unfortunately, as the healing progresses, a rigid plate can cause cortical bone to atrophy. This stress protection atrophy results in loss of bone mass and remodeling of cortical bone to incompletely mineralized bone. Nor is the remodeling confined to bone directly beneath the plate. It can be observed to a lesser extent in the cortex opposite the plate. The long term result of stress protection is a mechanically inferior bony structure in the region of the plate. Upon removal of the plate, refracture is often a possibility thereby requiring protection and limited activity until sufficient bone strength can be regained.

The use of intermediately stiff plating devices has also been proposed. This compromise solution results in some loss of initial stability with the attendant possibility of non-union. In return there is some long term reduction in stress protection atrophy.

Ideally, the bone fixation plate should be sufficiently strong to promote osseous union at the fracture site and sufficiently flexible to allow at least partial load transference to the fractured bone inasmuch as some loading enhances the healing process.

With respect to the repair of damaged ligaments and tendons it has recently been demonstrated by Jenkins et al, "Induction of Tendon and Ligament Formation by Carbon Implants", *J. Bone and Joint Surg.*, 59-B:53–57, 1977, and Wolter et al, "Ligament Replacement in the Knee Joint with Carbon Fibers Coated with Pyrolytic Carbon", *Trans. 3rd Ann. Mtg., Soc. for Biomat.*, 126, 1977, that ligaments and tendons can be replaced by filamentous carbon implants. New fibrous tissue grows and is gradually aligned, replacing the carbon scaffold which fractures and degrades mechanically.

Alexander et al, "Carbon-Polymer Composites for Tendon and Ligament Replacement", *Trans. 4th Ann. Mtg., Soc. for Biomat.*, 123, 1978, have indicated the need for physically protecting the delicate carbon fibers to avoid difficulty in implantation, premature fracturing in vivo and migration of carbon fibers from the site of surgery.

Kulnari et al, "Polylactic Acid for Surgical Implant", *Arch. Sug.*, 93, 839–843, 1966, and Cutright et al, "Tissue Reaction to the Biodegradable Polylactic Acid Suture", *Oral. Surg.*, 31: 134–139, 1971, have demonstrated the biocompatibility, biodegradability and ease of manufacture of surgical appliances of polylactic acid polymers.

U.S. Pat. Nos. 4,127,902 and 3,971,670 describe structures for in vivo implantation as substitutes for ligaments and tendons comprising a bio-compatible film, a bio-compatible fabric having a weave with no permanent yield in one direction integral with the film and a bio-compatible porous material which promotes the ingrowth of living tissues. The structure is used as a patch for repairing damaged ligaments and tendons and is designed to promote the growth of new ligament and tendon tissue. The patch, however, is intended for permanent implantation in the host animal.

U.S. Pat. No. 3,276,448 discloses the concept of coating a non-absorbable fiber-containing fabric intended for use as a repair structure for damaged tissue with collagen. The collagen is said to serve as a stimulus for new tissue growth in the area of repair.

It has been proposed in U.S. Pat. No. 3,992,725 to utilize carbon fibers as in vivo implantation material due to its ability to foster new tissue growth by virtue of its bio-compatibility. The patent proposes to combine the carbon fibers with polytetrafluoroethylene bonding material to provide a relatively permanent implant material.

U.S. Pat. No. 3,463,158 discloses the use of composites of polyglycolic acid and non-absorbable fibrous material as implants for tissue repair or replacement. The composition is designed such that new tissue growth surrounds the non-absorbable fibrous material.

U.S. Pat. No. 3,893,196 describes a material for fabricating a prosthesis comprising graphite fibers embedded in a coating with a medically inert plastic.

U.S. Pat. No. 3,272,204 discloses an absorbable collagen prosthetic implant reinforced with strands of non-absorbable material.

As is apparent from the aforesaid references, the use of filamentous carbon as an implant material is not unique. Indeed, it has been demonstrated that new fibrous tissue growth is encouraged by the carbon filaments, with the new tissue gradually aligning and replacing the carbon scaffold which fractures and degrades mechanically. However, filamentous carbon is usually produced on a polymer base, often with the addition of polymer sizing agents. These polymers frequently exhibit adverse tissue reactions or are carcinogens; as is polyacrylonitrile, a commonly used base material. It has been suggested to remove the sizing agent with methyl ethyl ketone possibly leaving trace polymer material behind. Complete removal of the sizing and base residue by heating to 4000° F. results in a strong material that is, unfortunately, brittle and sensitive to shear and bending deformations. In addition, unprotected carbon has been found to break up during implantation and migrate from its implantation area. In some cases, it forms sinus tracks right through the skin.

The mere mechanical reinforcement of the carbon fibers with other materials does not satisfactorily eliminate the migration problem.

It is an object of the invention to provide a composition, surgical article and method for the fabrication of the surgical article and a surgical method for repairing or replacing a part of the body of a human or non-human animal, wherein the said article promotes and provides a scaffold for the growth of new tissue but is substantially non-migratory and bio-absorbable.

SUMMARY OF THE INVENTION

The invention comprises a bio-compatible composition suitable for constructing a surgical article for the repair or replacement of a part of the body of a human or non-human animal comprising a composite of a bio-absorbable polymer and at least one substrate of a plurality of carbon fibers.

The invention also comprises a bio-compatible surgical article suitable for incorporation in the body of a human or non-human animal for the repair or replacement of a part thereof wherein the article is constructed of the above-described composition.

The invention includes a method for the manufacture of the bio-compatible surgical article comprising:

(a) providing at least one substrate of a plurality of carbon fibers;

(b) coating said at least one substrate with a bio-absorbable polymer, and, (c) shaping said at least one substrate into a surgical article of suitable shape and size.

The invention also includes a surgical method for the repair or replacement of a part of the body of a human or non-human animal by incorporating therein the above-described surgical article.

DETAILED DESCRIPTION OF THE INVENTION

Where the ultimate implant article is to be utilized for the repair or replacement of damaged tendons, ligaments or other fibrous tissue, the longitudinal axes of the carbon fibers are preferably oriented in substantially the same direction, i.e., parallel to the longitudinal axis of the fibrous tissue to be repaired or replaced in order to promote the proper orientation of the new fibrous tissue growth.

Where the article is to be used as, for example, a bone fixation plate the orientation of the carbon fibers is relatively unimportant, except from a strength standpoint, since the function of the carbon fibers is not to promote new fibrous tissue growth but to stabilize the bone.

It has been found that completely enveloping the carbon fiber scaffold with a bio-absorbable polymer effectively prevents the migration of the filamentous carbon after implantation. The bio-absorbable nature of the polymer prevents its interference with the new tissue growth promoting characteristics of the carbon fiber scaffold. The polymer functions as a mechanical reinforcer for the carbon fibers during tissue growth. In the case of fibrous tissue repair, new fibrous tissue grows and orients itself along the longitudinal axes of the carbon fibers. In the case of bone repair the composite is of sufficient strength to stabilize the bone and promote osseous union. The surgical article may be designed such that the rate of absorption of the bioabsorbable polymer by the body substantially coincides with the rate of new tissue growth, thereby enabling a transference of load from the carbon fiber-polymer composite to the new tissue over extended periods of time. It has been found that this transference of load during tissue growth is essential to the health and stability of the new tissue.

Any suitable bio-compatible and absorbable polymer may be utilized in the composition, article and method of the invention. Suitable such polymers include polyglycolic acid, collagen and polylactic acid. Polylactic acid is particularly preferred. Polylactic acid biodegrades by undergoing hydrolytic de-esterification to lactic acid, a normal intermediate in the lactic acid cycle of carbohydrate metabolism. The polymer is a thermoplastic and can be dissolved readily in chloroform and other suitable solvent materials. Polylactic acid is capable of maintaining its mechanical integrity in vivo for up to nine months, depending upon its mass, thickness, etc.

Any of the readily available carbon fibers may be employed in the composition, article and method of the invention provided that its tensile strength ranges from about 1.5 to about 2.75 GPa; its tensile modulus ranges from about 100 to about 500 GPa; and its ultimate elongation from about 0.4 to about 3.0%. Carbon fibers having a diameter in the range of from about 5 to about 15 microns, preferably about 10 microns, are satisfactory for preparation of the implant materials. It is particularly preferred to fabricate the implantation composition and articles from continuous tows or bundles containing approximately 10,000 carbon fibers. Generally, the tows or bundles are arranged in any suitable shape or configuration and sprayed, coated or drawn through a solution of the bio-absorbable polymer such that the substrate is completely enveloped by the polymer upon drying.

Depending, of course, upon the ultimate use of the article prepared from the composite, the latter may contain from about 30 to about 90%, preferably about 80%, by weight, of carbon fibers for ligament and tendon replacement and preferably about 50%, by weight, for fracture fixation device. The composite may be considered as a carbon fiber substrate coated with the bio-absorbable polymer or as the bio-absorbable polymer filled with carbon fibers.

It is essential for the repair or replacement of fibrous tissue that the logitudinal axes of the carbon fibers be oriented in substantially the same direction in order to ensure proper orientation of the new tissue growth upon implantation of the surgical article. For example, it has been found that composites prepared from carbon fibers in mesh or random orientation form, while promoting new tissue growth, gives rise to new tissue which is improperly oriented and, therefore, unstable.

The substrate of carbon fibers may take any suitable shape or size, depending upon its intended surgical use. For repair of ligaments and tendons, each of the substrates generally comprises a substantially uniplanar layer of carbon fibers. Where the ultimate article is used for bone fixation, the substrate is generally shaped so as to engage flush substantial areas of the exterior surface of the fractured bone. For the fixation of the long bones of the body, the contact surface is generally the internal curved surface of the fixation element adapted to engage the convex exterior surface of the long bone.

In order to provide maximum strength and to ensure proper tissue growth and orientation, it is preferred to form the article from a plurality of the coated carbon fiber substrate layers in a stacked relationship, each of the layers being separated from the next adjacent layer by a coating of the bio-absorbable polymer. It will be understood also that where the article is to be utilized for the repair or replacement of fibrous tissue, the longitudinal axes of the carbon fibers in each layer are aligned in the same direction. The stacked configuration of composite elements can be heated to a temperature slightly above the melting or fusing point of the bio-absorbable polymer in order to fuse or weld the layers together and the composite cooled in order to form the unitary product.

Where the surgical article is intended for the replacement or repair of non-fibrous tissue such as in the fixation of fractured bones, the particular orientation of the carbon fibers is not critical with respect to the orientation of new tissue. However, the carbon fibers should be aligned so as to provide maximum strength in the final article.

Where the article comprises stacked layers of polymer coated fiber substrates, the longitudinal axes of the carbon fibers in each layer are oriented in the same direction and form an angle of from 0° to 45°, preferably 15°, with the longitudinal axes of the carbon fibers in the next adjacent layer in order to provide maximum strength in the final article.

The surgical article or implant material is then preferably cut from the thus stacked composite in the desired shape or configuration. It will be understood by those skilled in the art, however, that the surgical article may be formed in the desired shape and/or configuration in a suitable mold or other shaping zone.

As noted above, the composite layers for forming tendon and ligament replacement articles are generally uniplanar in shape whereas those intended for bone fixation plates are generally designed so as to fit flush on the external surface of the fractured bone. The most preferred method for forming bone fixation plates is to stack the layers of composite material in a mold conforming to the bone surface to be treated and heating the assembly to a temperature above the melting point of the polymers to fuse the layers together. Upon cooling, the article is removed from the mold and cut and/or machined into the final desired shape.

Where the article is to be utilized as a bone fixation plate, it may be provided with apertures for biocompatible screws or other securing means for affixing the plate to the fractured bone surface.

The implant articles may be incorporated in the body of human and non-human animals according to standard and well-known techniques. For example, where the article comprises a bone fixation plate, the plate is affixed to the fractured bone utilizing screws or other securing means according to standard surgical techniques. Where the article comprises a replacement tendon or ligament, the article is affixed to the damaged ligament or tendon according to standard procedures. For example, in repairing damaged tendons, the replacement article may be threaded through a drill hole in the appropriate bone and secured to the appropriate area of the tendon to be repaired.

DESCRIPTION OF THE DRAWINGS

In FIG. 1, a polymer-carbon fiber composite is shown in the shape of a tendon 1 for the total replacement of a patella tendon in a human knee joint 3. The tendon replacement is affixed through drill holes 2 in the bone and by suturing through the soft tissue of the tendon.

In FIG. 2, a long bone B showing a fracture at 5 is stabilized with bone fixation plate 4 by securing the plate to the bone with screws 6. After osseus union at the fracture site and bio-absorption of the polymer, the screws may be surgically removed.

In FIGS. 3 and 4, each composite layer generally designated 8 of the exploded bone fixation plate contains a substrate of carbon fibers 12 enveloped by biocompatible polymer 10. In stacked configuration, the logitudinal axes of the carbon fibers 12 form an angle of about 15° with the longitudinal axes of the fixation plate and 30° to the axes of the carbon fibers in the next adjacent layer.

EXAMPLE 1

Figure 1:
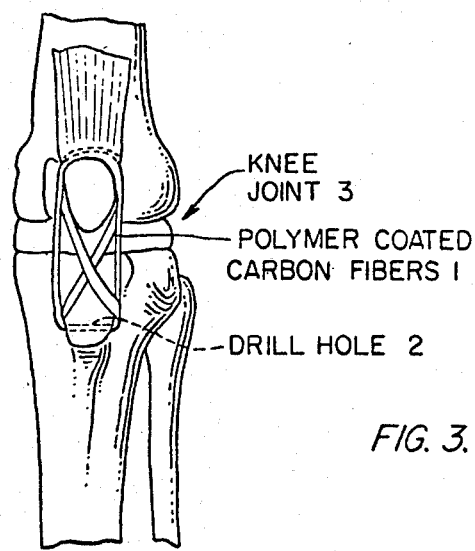
FIG. 1 is a partial fragmentary view of the human knee joint showing the total replacement of the patella tendon with the composite article of the invention.
Figure 2:
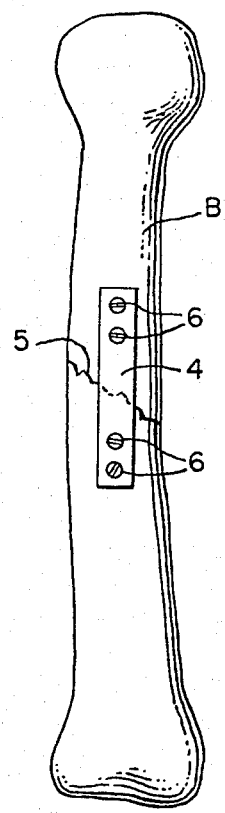
FIG. 2 is an elevational view of a fractured long bone fixated with the composite article of the invention.
Figure 3:
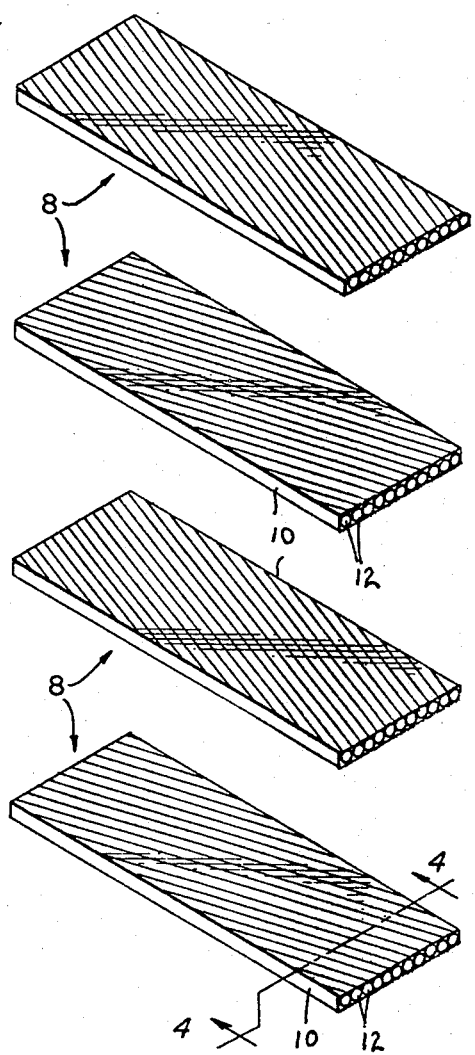
FIG. 3 is a greatly enlarged, exploded perspective view of a portion of a bone-fixation composite of a plurality of layers of polymer coated carbon fiber substrates.
Figure 4:
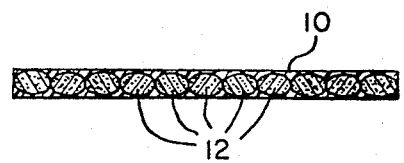
FIG. 4 is a cross-sectional view taken along the line 4—4 of FIG. 3.

A filamentous carbon fiber tow containing approximately 10,000 carbon fibers each having a thickness of about 10 microns were sprayed with a dilute chloroform solution of polylactic acid polymer to completely coat the fiber bundle. After drying, the coated substrates provided a replacement tendon structure suitable for repairing the patella tendon of adult Beagle dogs and white New Zealand rabbits. The patella tendon of one leg of each of the animals was removed and replaced by the polylactic acid polymer coated filamentous carbon composite articles which were threaded through a drill hole in the tibia and sutured through the quadraceps tendon above the patella.

The animals were left unprotected and allowed to freely move in their cages. Upon sacrifice at two months, the patella tendon replacement was freely movable, the carbon being contained and infiltrated within the developing fibrous tissue which was strongly attached to the bone and soft tissue. Histology on the replacement tissue indicated that the tissue was highly aligned in the direction of the carbon fibres showing evidence of good vascularity and mature tendon-like tissue formation.

After a period of four months, the animals had completely regained all function in the affected leg. There was no evidence of pain or walk with a limp. The ligament and tendon replacement provides mechanical strength upon implantation and allows ingrowth of new fibrous tissue, including bone attachment, with an increase in the transference of load to the new tissue as it develops.

EXAMPLE 2

An implant article suitable for use as a bone fixation plate was prepared according to the following procedure. A filamentous carbon fiber tow composed of approximately 10,000 carbon fibers each having a thickness of about 10 microns was wound on a cylindrical frame. The wound carbon fibers were spray coated with a chloroform solution of polylactic acid to provide a coated substrate comprising about 50%, by weight, of carbon fibers. Upon drying, the sheet of polymer coated carbon was removed and cut into the general elongate shape normally utilized as bone fixation plates. Twenty-four sheets of the coated carbon were stacked in a mold conforming to the shape of the fractured bone to be stabilized and molded into the appropriate bone fixation plate structure under pressure and at a temperature above the melting point of the polylactic acid polymer. The sheets were stacked such that the longitudinal axes of the carbon fibers in each sheet formed an angle of about 30° with the axes of the carbon fibers in the next adjacent sheet. Upon cooling, the resulting fused composite of carbon fibers and polylactic acid were provided with apertures for receiving bio-compatible screws for affixing the plate to the fractured bone.

The femurs of several white New Zealand rabbits were osteotomized and plated utilizing the above-described composite plates according to standard and conventional techniques. The animals were sacrificed over periods of three weeks and six weeks and the femurs evaluated grossly and histologically.

Examination revealed that osteoporosis of the bone under the plate is avoided. Since the fixation plate loses rigidity due to the bio-absorption of the polymer as the bone regains its strength thereby transferring load to the healing bone, the resulting healed bone bone does not show the stress protection which occurs with the utilization of steel and other metal fixation plates.

Inasmuch as the plate system is partially absorbed by the body, it need not be removed as is the case with conventional metal plates.

We claim:

1. A bio-compatible composition comprising a composite of a plurality of stacked substrates, each substrate comprising a plurality of carbon fibers completely enveloped by a bio-absorbable and bio-compatible polylactic acid polymer, wherein the weight ratio of carbon fibers to bio-absorbable and bio-compatible polymer is such that the said composite has sufficient strength and rigidity to form a surgical article therefrom especially adapted for the stabilization and repair or replacement of fractured bone tissue such that the rate of loss of the strength and rigidity of the composite due to absorption of the bio-absorbable polymer by the tissue substantially coincides with the rate of new bone tissue growth thereby enabling a gradual transference of load from the composite to new tissue in a human or non-human animal.

2. A bio-compatible surgical article of sufficient strength and rigidity and being of a size and shape adapted for the stabilization and repair or replacement of fractured bone tissue in a human or non-human animal comprising a bio-compatible composition comprising a composite of a plurality of stacked substrates, each substrate comprising a plurality of carbon fibers completely enveloped by a bio-absorbable and bio-compatible polylactic acid polymer, wherein the weight ratio of carbon fibers to bio-absorbable and bio-compatible polymer is such that the said composite has sufficient strength and rigidity and such that the rate of loss of the strength and rigidity of the composite due to absorption of the bio-absorbable polymer by the tissue substantially coincides with the rate of new bone tissue growth thereby enabling a gradual transference of load from the composite to new tissue.

3. The article of claim 2 wherein the longitudinal axes of carbon fibers in each substrate are oriented in the same direction and form an angle of between 0° and 45° with the longitudinal axes of the carbon fibers in the next adjacent substrate.

4. The article of claim 2, having a surface adapted to engage flush a substantial area of the exterior surface of a fractured bone on opposite sides of the fracture.

5. The article of claim 34, wherein the said surface is an international cylindrical surface adapted to engage flush the convex exterior surface of a fractured long bone.

6. The article of claim 3, wherein said angle is about 15°.

7. The article of claim 3, provided with means for securing said article to a part of said human or non-human animal.

8. The article of claim 7, wherein said means comprises bio-compatible screws for affixing said article to a fractured bone.

9. A method of fabricating a bio-compatible surgical article comprising providing a plurality of substrates, each comprising a plurality of carbon fibers, enveloping each substrate with a bio-absorbable and bio-compatible polylactic acid polymer, stacking said plurality of polymer enveloped substrates to form a composite having a weight ratio of carbon fibers to polymer such that the composite has sufficient strength and rigidity for the stabilization and repair or replacement of fractured bone tissue and forming said composite into a surgical article of sufficient strength and rigidity and of a size and shape for incorporation in the body of a human or non-human animal for the stabilization and repair or replacement of fractured bone tissue.

10. The method of claim 9, wherein the said composite contains about 50%, by weight, of carbon fibers.

11. The method of claim 10, including the steps of assembling a plurality of said coated uniplanar layers in a stacked relationship and heating said assembly to a temperature sufficient to at least partially fuse said bio-compatible polymer and cooling to bond said plurality of layers into a single unitary structure.

12. The method of claim 11, wherein the longitudinal axes of the carbon fibers in each layer are oriented in the same direction and forms an angle of between 0° and 45° with the longitudinal axes of the carbon fibers in the next adjacent layer.

13. The method of claim 12, wherein said angle is about 15°.

14. In a method of stabilizing and repairing or replacing the fractured bone tissue of a human or non-human animal by incorporating therein a surgical article, the improvement wherein the surgical article comprises a bio-compatible composition comprising a composite of a plurality of stacked substrates, each substrate comprising a plurality of carbon fibers completely enveloped by a bio-absorbable and bio-compatible polylactic acid polymer, wherein the weight ratio of carbon fibers to bio-absorbable and bio-compatible polymer is such that the said composite has sufficient strength and rigidity and such that the rate of loss of the strength and rigidity of the composite due to absorption of the bio-absorbable polymer by the tissue substantially coincides with the rate of new bone tissue growth thereby enabling a gradual transference of load from the composite to new tissue.

15. The method of claim 14, wherein each of said substrates comprises a substantially uniplanar layer of carbon fibers.

16. The method of claim 15, wherein said composite comprises a plurality of said uniplanar layers in a stacked relationship, each of said layers being separated from the next adjacent layer by a layer of said bio-absorbable polymer.

17. The method of claim 16, wherein the longitudinal axes of the carbon fibers in each substrate are oriented in the same direction and form an angle of from 0° to 45° with the longitudinal axes of the carbon fibers in the next adjacent substrate.

18. The method of claim 17 for repairing a fractured bone comprising securing said article to said bone at sites on opposite sides of said fracture.

* * * * *

UNITED STATES PATENT AND TRADEMARK OFFICE
CERTIFICATE OF CORRECTION

PATENT NO. : 4,512,038
DATED : April 23, 1985
INVENTOR(S) : Harold Alexander; John R. Parsons, Irving D. Strauchler; and Andrew B. Weiss It is certified that error appears in the above—identified patent and that said Letters Patent is hereby corrected as shown below:

In claim 5, column 7, line 63, change "34" to --4--;

In claim 5, column 7, line 64, change "international" to --internal--;

In claim 12, column 8, line 31, change "forms" to --form--.

Signed and Sealed this

Twentieth Day of August 1985

[SEAL]

Attest:

DONALD J. QUIGG

Attesting Officer

Acting Commissioner of Patents and Trademarks